United States Patent
Josias et al.

(10) Patent No.: US 12,109,442 B2
(45) Date of Patent: Oct. 8, 2024

(54) ORAL CARE COMPOSITIONS AND METHODS OF USE

(71) Applicant: Colgate-Palmolive Company, New York, NY (US)

(72) Inventors: Wilbens Josias, North Plainfield, NJ (US); Richard Robinson, Belle Mead, NJ (US); Adam Pepperney, Easton, PA (US); Kimdra Smith-Webster, Williamstown, NJ (US)

(73) Assignee: Colgate-Palmolive Company, New York, NY (US)

( * ) Notice: Subject to any disclaimer, the term of this patent is extended or adjusted under 35 U.S.C. 154(b) by 317 days.

(21) Appl. No.: 15/539,230

(22) PCT Filed: Dec. 26, 2014

(86) PCT No.: PCT/US2014/072451
§ 371 (c)(1),
(2) Date: Jun. 23, 2017

(87) PCT Pub. No.: WO2016/105440
PCT Pub. Date: Jun. 30, 2016

(65) Prior Publication Data
US 2017/0348550 A1 Dec. 7, 2017

(51) Int. Cl.
| | | |
|---|---|---|
| A61Q 11/00 | (2006.01) |
| A61K 8/19 | (2006.01) |
| A61K 8/24 | (2006.01) |
| A61K 8/27 | (2006.01) |
| A61K 8/34 | (2006.01) |
| A61K 8/44 | (2006.01) |
| A61K 8/46 | (2006.01) |
| A61K 8/49 | (2006.01) |

(52) U.S. Cl.
CPC ............ *A61Q 11/00* (2013.01); *A61K 8/19* (2013.01); *A61K 8/24* (2013.01); *A61K 8/27* (2013.01); *A61K 8/34* (2013.01); *A61K 8/44* (2013.01); *A61K 8/466* (2013.01); *A61K 8/49* (2013.01)

(58) Field of Classification Search
CPC ... A61K 8/19; A61K 8/24; A61K 8/27; A61K 8/34; A61K 8/44; A61K 8/466; A61K 8/49; A61Q 11/00
USPC .......................................................... 424/49
See application file for complete search history.

(56) References Cited

U.S. PATENT DOCUMENTS

| | | | |
|---|---|---|---|
| 9,486,396 B2 | 11/2016 | Maloney et al. | |
| 10,058,493 B2 | 8/2018 | Manus et al. | |
| 2006/0039939 A1* | 2/2006 | Lai | C08F 2/38 424/401 |
| 2009/0202454 A1 | 8/2009 | Prencipe et al. | |
| 2010/0330003 A1 | 12/2010 | Robinson et al. | |
| 2013/0022554 A1* | 1/2013 | Engel | A61Q 11/00 424/53 |
| 2013/0071456 A1 | 3/2013 | Fruge et al. | |
| 2013/0224126 A1 | 8/2013 | Lewus et al. | |
| 2013/0230469 A1 | 9/2013 | Lewus et al. | |
| 2013/0287709 A1 | 10/2013 | Maloney et al. | |
| 2015/0297500 A1 | 10/2015 | Robinson et al. | |
| 2015/0313813 A1 | 11/2015 | Rege et al. | |
| 2016/0303010 A1 | 10/2016 | Prencipe et al. | |
| 2016/0338921 A1 | 11/2016 | Prencipe et al. | |
| 2017/0020795 A1 | 1/2017 | Maloney et al. | |
| 2018/0015016 A1 | 1/2018 | Huang et al. | |
| 2018/0021234 A1 | 1/2018 | Prencipe et al. | |
| 2018/0168960 A1 | 6/2018 | Manus et al. | |
| 2018/0271762 A1 | 9/2018 | Huang et al. | |
| 2018/0344596 A1 | 12/2018 | Manus et al. | |
| 2019/0038531 A1 | 2/2019 | Rege et al. | |

FOREIGN PATENT DOCUMENTS

| | | | |
|---|---|---|---|
| WO | WO 1995/034274 | 12/1995 | |
| WO | WO 2011/016982 | 2/2011 | |
| WO | WO 2011/162755 | 12/2011 | |
| WO | WO 2011/162756 | 12/2011 | |
| WO | WO 2012/064338 | 5/2012 | |
| WO | WO 2012/064341 | 5/2012 | |
| WO | WO-2014088575 A1 * | 6/2014 | ............... A61K 8/27 |
| WO | WO 2014/144891 | 9/2014 | |
| WO | WO 2015/094849 | 6/2015 | |

OTHER PUBLICATIONS fda.gov, 2012, "Annex VI List of preservatives allowed for use in cosmetic products Revised based on agreement of 17th ACSB Meeting ASEAN Cosmetic Documents 1 Annex VI List of Preservatives Which Cosmetic Products May Contain," http://www.fda.gov.ph/attachments/article/38607/Annex_VI_revised_as_per_17th_ACSB.pdf.

International Search Report and Written Opinion of the International Searching Authority in International Application No. PCT/US2014/072451, mailed Feb. 16, 2016.

Drake, et al., "Growth-inhibitory effect of pyrophosphate on oral bacteria", Oral Microbiol Immunol., 9(1):25-8 (1994).

Moon, et al., "Antibacterial Action of Polyphosphate on Porphyromonas gingivalis", Antimicrobial Agents and Chemotherapy, 55(2):806-812 (2011).

Lorencova, et al., "Antibacterial effect of phosphates and polyphosphates with different chain length", J Environ Sci Health A Tox Hazard Subst Environ Eng., 47(14):2241-5 (2012).

Obritsch, et al., "Antibacterial effects of long-chain polyphosphates on selected spoilage and pathogenic bacteria", J Food Prot., 71(7):1401-5 (2008).

* cited by examiner

Primary Examiner — Adam C Milligan

(57) ABSTRACT

This invention relates to oral care compositions comprising a basic amino acid or salt thereof, a zinc source, and a preservative, as well as to methods of using and of making these compositions.

6 Claims, No Drawings

ORAL CARE COMPOSITIONS AND METHODS OF USE

FIELD

This invention relates to oral care compositions comprising a basic amino acid or salt thereof, a mixture comprising zinc oxide and zinc citrate, and a preservative to prevent microbial contamination, as well as to methods of using and of making these compositions.

BACKGROUND

Oral care compositions present particular challenges in preventing microbial contamination. Arginine and other basic amino acids have been proposed for use in oral care and are believed to have significant benefits in combating cavity formation and tooth sensitivity.

Commercially available arginine-based toothpaste, such as ProClude® toothpaste or DenClude® toothpaste, for example, contains arginine bicarbonate and precipitated calcium carbonate, but not fluoride. The carbonate ion is believed to have cariostatic properties, and the calcium is believed to form in complex with arginine to provide a protective effect.

However, the formulation of certain oral care compositions presents special challenges. For example, oral care compositions comprising arginine or basic amino acids may have a basic pH, increasing potential for microbial contamination compared to acidic formulations. Moreover, not all preservatives are active at higher pH. Some preservatives negatively affect the taste or aesthetics of the product. While certain preservatives, such as ethanol or parabens, are known to be effective at a range of pHs, these preservatives are not suitable for all products or all markets.

Zinc is a well-known antimicrobial agent used in toothpaste compositions. At effective concentrations, zinc has been shown to inhibit bacterial glycolysis and the activity of bacterial proteases. Zinc is also a well-known essential mineral for human health, and has been reported to help strengthen dental enamel and to promote cell repair. Unfortunately, conventional toothpaste formulations often require a high concentrations of zinc, e.g., 2% by weight or more, to achieve efficacy. At this concentration, the zinc imparts a notably astringent taste to the composition. There is thus a need for improved antibacterial toothpaste formulations that do not suffer from the drawbacks of conventional compositions.

Accordingly, there is a need for improved preservative agents for use in oral compositions comprising basic amino acids.

BRIEF SUMMARY

It has been surprisingly found that the inclusion of a zinc oxide and/or zinc citrate, selected at certain concentrations and amounts, unexpectedly increase the antibacterial effect of oral care compositions comprising an amino acid, e.g., arginine, in the oral cavity of a user. The current formulations offer the advantage of robust microbial protection without significantly interfering with the stability of the oral care composition and by allowing for formulations which use less zinc—which may have undesirable aesthetic qualities (e.g., poor taste). Without being bound by any theory, it is believed that the presence of the amino acid may help to increase the amount of soluble zinc which can then have an unexpected increased effect on inhibiting bacterial growth in the oral cavity of a user.

The invention contemplates an oral care composition (Composition 1.0) comprising:
   i. an effective amount of a basic amino acid, in free or salt form (e.g., arginine);
   ii. an of amount of a mixture comprising zinc oxide and zinc citrate
   iii. an effective amount of a preservative, wherein the preservative is selected from the group consisting of:
      a. benzyl alcohol;
      b. methylisothiazolinone ("MIT");
      c. Sodium bicarbonate;
      d. sodium methyl cocoyl taurate (tauranol);
      e. polyphosphate;
      and combinations of any of the preservatives a.-e., thereof.

For example, the invention contemplates an of the following compositions (unless otherwise indicated, values are given as percentage of the overall weight of the composition):

1.1 Composition 1.0 wherein the basic amino acid is arginine, lysine, serine, citrullene, ornithine, creatine, histidine, diaminobutanoic acid, diaminoproprionic acid, salts thereof and/or combinations thereof 1.2 Composition 1.0 or 1.1 wherein the basic amino acid has the L-configuration.

1.3 Any of the preceding compositions wherein the basic amino acid is provided in the form of a di- or tri-peptide comprising the basic amino acid, or salts thereof.

1.4 Any of the preceding compositions wherein the basic amino acid is present in an amount corresponding to 1% to 15%, e.g., 3% wt. to 10% wt. of the total composition weight, e.g., about 8% wt. the weight of the basic amino acid being calculated as free base form.

1.5 Any of the preceding compositions wherein the basic amino acid is arginine. (e.g., 6%-10% wt., e.g., 8%)

1.6 Any of the preceding compositions wherein the basic amino acid is L-arginine.

1.7 Any of the preceding compositions wherein the basic amino acid is partially or wholly in salt form.

1.8 Composition 1.8 wherein the basic amino acid is arginine phosphate.

1.9 Composition 1.8 wherein the basic amino acid is arginine hydrochloride.

1.10 Composition 1.8 wherein the basic amino acid is arginine bicarbonate.

1.11 Any of the preceding compositions wherein the basic amino acid is ionized by neutralization with an acid or a salt of an acid.

1.12 Any of the foregoing compositions wherein the benzyl alcohol is present from 0.6-0.9% wt., e.g. about 0.7%.

1.13 Any of the foregoing compositions wherein the polyphosphate is pyrophosphate, tripolyphosphate or hexametaphosphate, e.g., in salt form, e.g., sodium or potassium salt form, e.g., in an amount of from 0.1-3%.

1.14 The composition of 1.25, wherein the polyphosphate is a pyrophosphate, and wherein the pyrophosphate is tetrasodium pyrophosphate 1.15 The composition of 1.26, wherein the tetrasodium pyrophosphate is in an amount of 0.2%-1.0% (e.g., 0.5% by wt.)

1.16 Any of the preceding compositions, wherein methylisothiazolinone is present in from 0.01%-0.05% wt. (0.01%, 0.03%, or 0.05%)

1.17 Any of the preceding compositions, wherein sodium bicarbonate is present from 0.5%-2.0% wt. (e.g., 1.0% wt.)
1.18 Any of the preceding compositions, wherein sodium methyl cocoyl taurate (tauranol) is present from 1.0%-2.0% wt.
1.19 Any of the foregoing compositions wherein the composition is ethanol-free.
1.20 Any of the preceding compositions further comprising a fluoride source e.g., a soluble fluoride salt).
1.21 The composition of 1.25, wherein the fluoride source is a soluble fluoride salt selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
1.22 Any of the preceding compositions wherein the fluoride source is a fluorophosphate.
1.23 Any of the preceding compositions wherein the fluoride source is sodium monofluorophosphate.
1.24 Any of the preceding compositions wherein the fluoride source is a fluoride salt present in an amount of 0.1 wt. % to 2 wt. % of the total composition weight.
1.25 Any of the preceding compositions wherein the fluoride source is a soluble fluoride salt present in the amount of about 1.1% by weight of the composition.
1.26 Any of the preceding compositions wherein the fluoride source is a soluble fluoride salt which provides fluoride ion in an amount of from 50 to 25,000 ppm (e.g., 750-2000 ppm, e.g., 1000-1500 ppm, e.g., about 1000 ppm, e.g., about 1450 ppm)
1.27 Any of the preceding compositions wherein the pH is between 7.5 and 10.5, e.g., 9.0 to 10.0, e.g., 9.4.
1.28 Any of the preceding compositions further comprising calcium carbonate.
1.29 The composition of 1.33, wherein the calcium carbonate is a precipitated calcium carbonate high absorption (e.g., 20% to 30% by weight of the composition) (e.g., 25% precipitated calcium carbonate high absorption).
1.30 The composition of 1.34, further comprising a precipitated calcium carbonate—light (e.g., about 10% precipitated calcium carbonate—light) (e.g., about 10% natural calcium carbonate).
1.31 Any of the preceding compositions further comprising an abrasive or particulate (e.g., silica).
1.32 Any of the preceding compositions, wherein the nonionic surfactant, is in an amount of from 0.5-5%, e.g, 1-2%, selected from poloxamers e.g., poloxamer 407), polysorbates (e.g., polysorbate 20), polyoxyl hydrogenated castor oil (e.g., polyoxyl 40 hydrogenated castor oil), and mixtures thereof.
1.33 Any of the preceding compositions wherein the sorbitol is in a total amount of 10-40% (e.g., about 23%).
1.34 Any of the preceding compositions, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1 or 4:1).
1.35 Any of the preceding compositions, wherein the zinc citrate is in an amount of from 0.25 to 0.75 wt % (e.g., 0.5%) and zinc oxide may be present in an amount of from 0.75 to 1.25 wt % (e.g., 1.0%) based on the weight of the oral care composition.
1.36 Any of the preceding compositions comprising polymer films.
1.37 Any of the preceding compositions comprising flavoring, fragrance and/or coloring.
1.38 The composition of 1.50, wherein the flavoring agent is sodium saccharin, sucralose, or a mixture thereof.
1.39 Any of the preceding compositions comprising from 5%-35%, e.g., 10%-20%, e.g., 15%, water.
1.40 Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), beuzalkonium chloride, tetradecylpyridinium chloride (TPC), N-tetradecyl-4-ethylpyridinium chloride (TDEPC)), phenolic antiseptics, hexetidine, octenidine, sanguinarine, povidone delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, dehnopinol, octapinol and other piperidino derivatives, nicin preparations, chlorite salts; and mixtures of any of the foregoing.
1.41 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.
1.42 Any of the preceding compositions comprising a whitening agent.
1.43 Any of the preceding compositions comprising a whitening agent selected from a whitening active selected from the group consisting of peroxides, metal chlorites, perborates, percarbonates, peroxyacids, hypochlorites, and combinations thereof.
1.44 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.
1.45 Any of the preceding compositions further comprising an agent that interferes with or prevents bacterial attachment, e.g., ELA or chitosan.
1.46 Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.47 Any of the preceding oral compositions, wherein the oral composition may be any of the following oral compositions selected from the group consisting of: a toothpaste or a dentifrice, a mouthwash or a mouth rinse, a topical oral gel, and a denture cleanser.

1.48 A composition obtained or obtainable by combining the ingredients as set forth in any of the preceding compositions.

1.49 Any of Composition 1.0, and 1.1-1.53, wherein the composition is a dentifrice comprising:
  a. 3%-15% by wt. of arginine bicarbonate
  b. 20%-30% of precipitated calcium carbonate (PCC) (e.g., precipitated calcium carbonate high absorption);
  c. 5%-15% of a natural calcium carbonate (e.g., limestone)
  d. 6%-10% benzyl alcohol by wt. (e.g., about 7% by wt. benzyl alcohol)
  e. 0.1%-1.0% zinc citrate trihydrate
  f. 0.5%-1.5% zinc oxide
  g. 0.5%-3% non-ionic surfactant (e.g., Poloxamer 407 (plutonic) (e.g., about 1.5% by wt.)
  h. 20%-30% of sorbitol (e.g., 23% by wt.)

A composition obtained or obtainable by combining the ingredients as set forth in any of the preceding compositions.

In another embodiment, the invention encompasses a method to improve oral health comprising applying an effective amount of the oral composition of an of the embodiments set forth above to the oral cavity of a subject in need thereof, e.g., a method to
  i. reduce or inhibit formation of dental caries,
  ii. reduce, repair or inhibit early enamel lesions, e.g., as detected by quantitative light-induced fluorescence (QLF) or electrical caries measurement (ECM),
  iii. reduce or inhibit demineralization and promote remineralization of the teeth,
  iv. reduce hypersensitivity of the teeth,
  v. reduce or inhibit gingivitis,
  vi. promote healing of sores or cuts in the mouth,
  vii. reduce levels of acid producing bacteria,
  viii. to increase relative levels of arginolytic bacteria,
  ix. inhibit microbial bio film formation in the oral cavity,
  x. raise and/or maintain plaque pH at levels of at least pH 5.5 following sugar challenge,
  xi. reduce plaque accumulation,
  xii. treat dry mouth,
  xiii. enhance systemic health, including cardiovascular health, e.g., by reducing potential for systemic infection via the oral tissues,
  xiv. whiten teeth,
  xv. reduce erosion of the teeth,
  xvi. immunize (or protect) the teeth against cariogenic bacteria and their effects, and/or
  xvii. clean the teeth and oral cavity.

The invention further comprises the use of sodium bicarbonate, sodium methyl cocoyl taurate (taurano), methylisothiazolinone (MIT), and beazyl alcohol and combinations thereof in the manufacture of a composition of the invention, e.g., for use in any of the indications set forth in the above method of Composition 1.0, et seq.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively the oral composition may be dual phase dispensed from a separated compartment dispenser.

Basic Amino Acids

The basic amino acids which can be used in the compositions and methods of the invention include not only naturally occurring basic amino acids, such is arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source

The oral care compositions may further include one or more fluoride ion sources, e.g., soluble fluoride salts. A wide variety of fluoride ion-yielding materials can be employed as sources of soluble fluoride in the present compositions.

Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride sodium fluoride, potassium fluoride, sodium monofluorophosphate, sodium fluorosilicate, ammoniumiluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely conically bound, e.g., as in sodium fluoride.

Surfactants

The invention may in some embodiments contain anionic surfactants, e.g., the Compositions of Composition 1.0, et seq., for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_6$-$_30$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates polysorbate 20), polyoxyl hydrogenated castor oils (e.g., polyoxyl 40 hydrogenated castor oil), and mixtures thereof.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.5 wt. % pyrophosphate ions, 0.9-3 wt. %.

The pyrophosphates also contribute to preservation of the compositions by lowering water activity.

Polymers

The oral care compositions of the invention also optionally include one or more polymers, such as polyethylene glycols, polyvinylm ethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymer of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon oletinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, othacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially relined to remove impurities. For use in the present invention, the material has an average particle size of less than 10 microns, e.g., 3-7 microns, e.g. about 5.5 microns. Because natural calcium carbonate may contain a high proportion of relatively large particles of not carefully controlled, which may unacceptably increase the abrasivity preferably no mote than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be convened back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g. having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate, and/or silica abrasives such as precipitated silicas having a mean particle size of up to about 20 μm, such as Zeodent 115, marketed by J. M. Huber, sodium metaphosphate, potassium metaphosphate, aluminum silicate, calcined alumina, bentonite or other siliceous materials, or combinations thereof. However the additional abrasives are preferably not present in a type or amount so as to increase the RDA of the dentifrice to levels which could damage sensitive teeth, e.g., greater than 130.

Enzymes

The oral care compositions of the invention may also optionally include one or more enzymes. Useful enzymes include any of the available proteases, glucanohydrolases, endoglycosidases, amylases, mutanases, lipases and mucinases or compatible mixtures thereof In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes 0.002% to 2.0% in one embodiment or 0.05% to 1.5% in another embodiment or in yet another embodiment 0.1% to 0.5%.

Water

Water is present in the oral compositions of the invention. Water, employed in the preparation of commercial oral compositions should be deionized and free of organic impurities. Water commonly makes up the balance of the compositions and includes 10% to 90%, e.g., 40% to 70% by weight of the oral compositions. This amount of water includes the free water which is added plus that amount which is introduced with other materials such as with sorbitol or any components of the invention.

Humectants

Within certain embodiments of the oval compositions, it is also desirable to incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 10% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein.

The present invention in its method aspect involves applying to the oral cavity a safe and effective amount of the compositions described herein.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline.

Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6-month treatments are made. In addition, a classical caries score for root surfaces is made using a tactile probe. The hardness is classified on a three-point scale: hard, leathery, or soft. In this type of study, typically the results are reported as electrical resistance (higher number is better) for the ECM measurements and an improvement in hardness of the lesion based on the tactile probe score.

Test methods for the desensitizing properties of the compositions described herein, uses the method described in U.S. Pat. No. 5,589,159, the disclosure of which is incorporated by reference herein in its entirety. This method measures the hydraulic conductance of materials, providing an objective reduction in fluid flow that correlates with reduction in fluid flow in dentinal tubules. In this method, intact human molars free from caries and restorations are sectioned perpendicularly to the long axis of the tooth with a metallurgical saw to form thin sections, or discs, from about 0.4 to about 0.8 mm thick. Sections containing dentin and free of enamel were selected for testing and then etched with citric acid solution to remove the smear layer. Each disc was mounted into a split chambered device described in J. Dent. Research, 57: 187 (1978) which is a special leak-proof chamber connected to a pressurized fluid reservoir containing a tissue culture fluid. By using a mixture of pressurized nitrogen and carbon dioxide gas, the fluid can be made at physiological pH. To further ensure accuracy, the discs were wetted with artificial saliva (phosphate buffer saline, PBS) to approximate intra-oral conditions. The apparatus includes a glass capillary tube attached to a flow sensor (FLODEC, DeMarco Engineering SA, Geneva). An air bubble is injected into the glass capillary tube. By measuring the displacement of the bubble as a function of time, fluid flow through the dentin disc can be measured. Fluid flow is equivalent to the dentin permeability.

The Compositions of the Invention are thus useful in a method to reduce early lesions of the enamel (as measured by QLF or ECM) relative to a composition lacking effective amounts of fluorine and/or arginine.

The Compositions of the invention are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least pH 5.5 following sugar challenge, reduce plaque accumulation, and/or clean the teeth and oral cavity.

Finally, by increasing the pH in the mouth and discouraging pathogenic bacteria, the Compositions of the Invention are useful to promote healing of sores or cuts in the mouth.

The compositions and methods according to the invention can be incorporated into oral compositions for the care of the mouth and teeth such as toothpastes, transparent pastes, gels, mouth rinses, sprays and chewing gum.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to Helicobacter, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1

Various formulations containing an anionic surfactant are tested to determine robustness to mold. Factors which are tested include:

Humectant: sorbitol vs. glycerin

Sodium N-silicate: present vs. absent

Benzyl alcohol: present vs. absent

Sweetener: saccharin vs. sucralose/acesulfame potassium

Formulations containing sorbitol provide better robustness than glycerin against mold. The addition of benzyl alcohol to the formulation also improves the robustness against mold. The addition of sweetener and the N-silicate does not negatively affect the robustness of the formulation.

Example 2

As shown in Table 1 below, various preservative systems containing a non-ionic surfactant are evaluated to determine the efficacy of the addition of: sodium bicarbonate at 1.5%, methylisothiazolinone (MIT), an increase in the level of benzyl alcohol to 0.7%, and sodium methyl cocoyl taurate (tauranol)

TABLE 1

| | Current | 0.7% Benzyl Alcohol | Increase Sodium Bicard to 1.5% | 0.01% MIT | 0.03% MIT | w/ 0.05% MIT |
|---|---|---|---|---|---|---|
| SORBITOL | 23.000 | 23.000 | 23.000 | 23.000 | 23.000 | 23.000 |
| XANTHAN GUM | 0.400 | 0.400 | 0.400 | 0.400 | 0.400 | 0.400 |
| SODIUM CMC | 0.600 | 0.600 | 0.600 | 0.600 | 0.600 | 0.600 |
| SODIUM SACCHARIN | 0.400 | 0.400 | 0.400 | 0.400 | 0.400 | 0.400 |
| SODIUM BICARBONATE | 0.500 | 0.500 | 1.500 | 1.000 | 1.000 | 1.000 |
| SODIUM MONOFLUOROPHOSPHATE | 1.100 | 1.100 | 1.100 | 1.100 | 1.100 | 1.100 |
| DEMINERALIZED WATER | 16.100 | 15.700 | 15.100 | 15.590 | 15.570 | 15.550 |
| ZINC CITRATE TRIHYDRATE | 0.500 | 0.500 | 0.500 | 0.500 | 0.500 | 0.500 |
| ZINC OXIDE | 1.000 | 1.000 | 1.000 | 1.000 | 1.000 | 1.000 |
| TETRASODIUM PYROPHOSPHATE | 0.500 | 0.500 | 0.500 | 0.500 | 0.500 | 0.500 |
| Precipitated Calcium Carbonate High Absorption | 25.000 | 25.000 | 25.000 | 25.000 | 25.000 | 25.000 |
| PRECIPITATED CALCIUM CARBONATE | 10.000 | 10.000 | 10.000 | 10.000 | 10.000 | 10.000 |
| TITANIUM DIOXIDE | 0.500 | 0.500 | 0.500 | 0.500 | 0.500 | 0.500 |
| Arginine-Bicarbonate solution | 13.860 | 13.860 | 13.860 | 13.860 | 13.860 | 13.860 |
| Cool Mint Blend Flavor | 1.400 | 1.400 | 1.400 | 1.400 | 1.400 | 1.400 |
| BENZYL ALCOHOL FCC | 0.300 | 0.300 | 0.300 | 0.300 | 0.300 | 0.300 |
| COCOAMIDOPROPYL BETAINE | 3.340 | 3.340 | 3.340 | 3.340 | 3.340 | 3.340 |
| Poloxamer 407 (Pluronic) | 1.500 | 1.500 | 1.500 | 1.500 | 1.500 | 1.500 |
| SODIUM METHYL COCOYL TAURATE ~95% | | | | | | |
| METHYLISOTHIAZOLINONE (MIT) | | | | 0.010 | 0.030 | 0.050 |
| Sodium Gluconate | | | | | | |
| Total | 100.00 | 100.00 | 100.00 | 100.00 | 100.00 | 100.00 |

Results:

| | 1.5% Taurarol & No MIT | 1.5% Taurarol & 0.01% MIT | 1.5% Taurarol & 0.03% MIT | 0.5% NaBicard, 1% NaGluconate | 0.5% NaBicard, 2% NaGluconate | 1% NaBicard, 2% NaGluconate |
|---|---|---|---|---|---|---|
| SORBITOL | 23.000 | 23.000 | 23.000 | 23.000 | 23.000 | 23.000 |
| XANTHAN GUM | 0.400 | 0.400 | 0.400 | 0.400 | 0.400 | 0.400 |
| SODIUM CMC | 0.600 | 0.600 | 0.600 | 0.600 | 0.600 | 0.600 |
| SODIUM SACCHARIN | 0.400 | 0.400 | 0.400 | 0.400 | 0.400 | 0.400 |
| SODIUM BICARBONATE | 1.000 | 1.000 | 1.000 | 0.500 | 0.500 | 1.000 |
| SODIUM MONOFLUOROPHOSPHATE | 1.100 | 1.100 | 1.100 | 1.100 | 1.100 | 1.100 |

TABLE 1-continued

| | | | | | | |
|---|---|---|---|---|---|---|
| DEMINERALIZED WATER | 17.940 | 17.930 | 17.910 | 15.100 | 14.100 | 13.600 |
| ZINC CITRATE TRIHYDRATE | 0.500 | 0.500 | 0.500 | 0.500 | 0.500 | 0.500 |
| ZINC OXIDE | 1.000 | 1.000 | 1.000 | 1.000 | 1.000 | 1.000 |
| TETRASODIUM PYROPHOSPHATE | 0.500 | 0.500 | 0.500 | 0.500 | 0.500 | 0.500 |
| Precipitated Calcium Carbonate High Absorption | 25.000 | 25.000 | 25.000 | 25.000 | 25.000 | 25.000 |
| PRECIPITATED CALCIUM CARBONATE | 10.000 | 10.000 | 10.000 | 10.000 | 10.000 | 10.000 |
| TITANIUM DIOXIDE | 0.500 | 0.500 | 0.500 | 0.500 | 0.500 | 0.500 |
| Arginine-Bicarbonate solution | 13.860 | 13.860 | 13.860 | 13.860 | 13.860 | 13.860 |
| Cool Mint Blend Flavor | 1.400 | 1.400 | 1.400 | 1.400 | 1.400 | 1.400 |
| BENZYL ALCOHOL FCC | 0.300 | 0.300 | 0.300 | 0.300 | 0.300 | 0.300 |
| COCOAMIDOPROPYL BETAINE | | | | 3.340 | 3.340 | 3.340 |
| Poloxamer 407 (Pluronic) | 1.000 | 1.000 | 1.000 | 1.500 | 1.500 | 1.500 |
| SODIUM METHYL COCOYL TAURATE ~95% | 1.500 | 1.500 | 1.500 | | | |
| METHYLISOTHIAZOLINONE (MIT) | | 0.010 | 0.030 | | | |
| Sodium Gluconate | | | | 1.000 | 2.000 | 2.000 |
| Total | 100.00 | 100.00 | 100.00 | 100.00 | 100.00 | 100.00 |

| % Mold Reduction | Current | 0.7% Benzyl Alcohol | Increase Sodium Bicard to 1.5% | MIT 0.01% | MIT 0.03% | MIT 0.05% |
|---|---|---|---|---|---|---|
| 7-Day | 54.38% | 99.65% | 90.00% | 96.32% | 99.95% | >90.0% |
| 14-Day | 94.42% | 99.99% | 99.23% | 99.79% | 99.95% | 99.94% |
| 21-Day | 96.67% | 99.86% | 97.50% | >90.0% | >90.0% | >90.0% |
| 28-Day | 99.92% | >90.0% | 99.87% | >90.0% | >90.0% | >90.0% |

| 1.5% Taurarol | | | Sodium Gluconate | | |
|---|---|---|---|---|---|
| No MIT | 0.01% MIT | 0.03% MIT | 0.05% NaBicarb, 1% NaGluconate | 0.05% NaBicarb, 2% NaGluconate | 1% NaBicarb, 2% NaGluconate |
| 86.49% | 93.68% | >90.0% | 79.30% | 89.65% | >90.0% |
| 94.33% | 99.98% | 99.94% | 94.50% | 95.17% | 94.08% |
| 99.74% | >90.0% | >90.0% | 98.75% | 97.58% | 98.08% |
| >90.0% | >90.0% | >90.0% | 99.96% | 99.84% | 99.75% |

The results demonstrate an increase in sodium bicarbonate assists with the reduction of mold. The addition of methylisothiazolinone (MIT) furthers assists with the reduction of mold. Although, tauranol alone did not help with the reduction of mold, but in conjunction with MIT the product meets an acceptable mold reduction criteria. The results also demonstrate that sodium gluconate at 2% and 1% sodium bicarbonate helps to achieve an acceptable mold reduction, while 2% sodium gluconate and 0.5% sodium bicarbonate does not.

Example 3

Table 2 shows a representative formulation according to the invention

| | (wt. %) |
|---|---|
| SORBITOL-NON-CRYSTALLIZING-70% SOLN. | 23.0 |
| XANTHAN GUM-USP or EP | 0.40 |
| SODIUM CMC-TYPE 12 | 0.60 |
| SODIUM SACCHARIN USP or EP | 0.25 |
| SUCRALOSE USP, FP | 0.02 |
| SODIUM MONOFLUOROPHOSPHATE-USP | 1.10 |
| DEMINERALIZED WATER | 15.73 |
| ZINC CITRATE TRIHYDRATE | 0.50 |
| ZINC OXIDE | 1.00 |
| TETRASODIUM PYROPHOSPHATE-FINE | 0.50 |
| SODIUM BICARBONATE-POWDERED-USP/EP | 0.50 |
| Precipitated Calcium Carbonate High Absorption | 25.00 |
| PRECIPITATED CALCIUM CARBONATE-LIGHT | 10.00 |
| TITANIUM DIOXIDE-FD & C GRADE | 0.50 |
| Arginine-Bicarbonate solution | 13.86 |
| CSPR Mint Flavor | 1.50 |
| COCAMIDOPROPYL BETAINE | 3.34 |
| Poloxomer 407 (Pluronic) | 1.50 |
| BENZYL ALCOHOL FCC | 0.70 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

What is claimed is:

1. An oral care composition comprising:
   arginine, in free or salt form;
   a mixture comprising zinc oxide and zinc citrate;
   a preservative, wherein the preservative is benzyl alcohol, wherein the benzyl alcohol is in an amount of 0.7% by wt., wherein the arginine is present in an amount of 1% to 15% wt. based on the weight of the oral care composition, the weight of the arginine being calculated as free base form, wherein zinc oxide is present in an amount of 1% wt. based on the weight of the oral care composition, and wherein the zinc citrate is in an amount of from 0.5% wt. based on the weight of the oral care composition; and
   wherein the pH of the oral care composition is between 7.5 and 10.5.
2. The oral care composition of claim 1, wherein the arginine is L-arginine.
3. The oral care composition of claim 1, wherein the arginine is present at about 8% wt.
4. The oral care composition of claim 1, wherein the ratio of zinc oxide to zinc citrate is 2:1.
5. The oral care composition of claim 1, wherein the composition further comprises tetrasodium pyrophosphate, and wherein the tetrasodium pyrophosphate is in an amount of 0.2%-1.0% wt. based on the weight of the oral care composition.
6. The oral care composition of claim 1, wherein the composition further comprises tetrasodium pyrophosphate, and wherein the tetrasodium pyrophosphate is in an amount of about 0.5% wt. based on the weight of the oral care composition.

* * * * *